United States Patent [19]

Bruchmann

[11] Patent Number: 5,149,766
[45] Date of Patent: Sep. 22, 1992

[54] PROCESS FOR THE PREPARATION OF URETDIONE GROUP CONTAINING POLYISOCYANATES

[75] Inventor: Bernd Bruchmann, Ludwigshafen, Fed. Rep. of Germany

[73] Assignee: BASF Aktiengesellschaft, Ludwigshafen, Fed. Rep. of Germany

[21] Appl. No.: 568,122

[22] Filed: Aug. 16, 1990

[30] Foreign Application Priority Data

Sep. 14, 1989 [DE] Fed. Rep. of Germany ....... 3930670

[51] Int. Cl.$^5$ ............................................... C08G 18/74
[52] U.S. Cl. .................................. 528/49; 252/182.2; 252/182.21; 528/73; 540/202; 548/951
[58] Field of Search .................. 252/182.2, 182.21; 528/49, 73; 540/202; 548/951

[56] References Cited

U.S. PATENT DOCUMENTS 3,357,939 12/1967 Reischl et al. ..................... 528/73

*Primary Examiner*—Maurice J. Welsh
*Assistant Examiner*—Rachel Johnson
*Attorney, Agent, or Firm*—Martin P. Connaughton

[57] ABSTRACT

The present invention relates to a process for the preparation of uretdione group containing polyisocyanates comprising reacting monomeric aromatic diisocyanates in the presence of 1,2-dimethylimidazole used as a catalyst in an inert organic solvent whereby the weight ratio of solvent to diisocyanate lies in a range of from 0.1:1 to 2:1.

2 Claims, No Drawings

PROCESS FOR THE PREPARATION OF URETDIONE GROUP CONTAINING POLYISOCYANATES

The present invention deals with a process for the preparation of uretdione group containing polyisocyanates, comprising reacting monomeric aromatic diisocyanates in the presence of 1,2-dimethylimidazole as a catalyst in an inert organic solvent.

It is generally known that uretdiones are prepared by reacting isocyanates in the presence of certain catalysts.

Richter and Ulrich in *Synthesis*, 1975, pg. 463, disclose a process in which benzyl isocyanates are reacted in the presence of 1,2-dimethylimidazole as a catalyst without a solvent, however, considerable quantities of isocyanurates result. Isocyanurates are undesirable for a number of applications since they are trifunctional and have a tendency to crosslink. In addition, the ten weight percent, based on the amount of isocyanate, of catalyst used here is worthy of improvement with respect to profitability.

Noack and Schwetlick in *Z. Chem.*, 26(1), pg. 117, 1986, report this disadvantage of the formation of isocyanurates. Only a 35% dimer yield is obtained when reacting T80, a mixture of 80 weight percent 2,4- and 20 weight percent to 2,6-toluene diisocyanate, with 1,2-dimethylimidazole as a catalyst in a mixture of dimethylethyl ketone and cyclohexane. Here, the weight ratio of the solvent mixture to diisocyanate is 3:1.

Using a mixture of different solvents in a commercial process is less suitable since reworking the solvents is expensive.

The object of the present invention was to overcome the aforesaid shortcomings.

Accordingly, a process for the preparation of uretdione group containing polyisocyanates was found by reacting monomeric aromatic diisocyanates in the presence of 1,2-dimethylimidazole used as a catalyst in an inert organic solvent whereby the weight ratio of solvent to diisocyanate lies in a range of from 0.1:1 to 2:1.

In addition, it was also discovered that toluene is especially effective as a solvent.

Typical monomeric aromatic diisocyanates are for example, 1,5-naphthalene diisocyanate, 4,4'-diphenylmethane diisocyanate, 1,4-phenylene diisocyanate as well as preferably 2,6-toluene diisocyanate and most preferably, 2,4-toluene diisocyanate and 4,4'-diphenylmethane diisocyanate. However, basically all aromatic monomeric diisocyanates can be used. It is understood that mixtures too of diisocyanates can be used.

The 1,2-dimethylimidazole used as a catalyst is used preferably in a quantity from 0.01 to 10 weight percent, more preferably 0.05 to 1 weight percent based on the isocyanate used.

The inert organic solvents used in the process of the present invention are known per se. Generally, all solvents are suitable which are inert to the starting materials, the catalysts and the final products. Trichloroethylene or n-hexane are preferred and most preferred is toluene. The weight ratio of the solvent mixture lies in a range of from 0.1:1 to 2:1 based on the weight of the isocyanate. Preferably used is a ratio of from 0.3:1 to 1:1.

The catalyst, also in solution, is added while stirring to the dissolved diisocyanate preferably at temperatures of from −10° C. to 80° C., more preferably at 20° C. to 50° C. The weight ratio of solvent lies in a range of from 1:1 to 100:1, more preferably 10:1 to 60:1 based on the weight of the 1,2-dimethylimidazole.

The reaction product formed is separated, washed and dried following a reaction time of preferably 2 to 48 hours, more preferably 14 to 21 hours at temperatures of preferably 20° to 100° C., more preferably 20° to 50° C.

The advantages realized with the present invention are that the content of undesirable isocyanurate is less than or equal to 2 percent and in spite of a low catalyst concentration high yields of uretdione group containing polyisocyanates are obtained.

The uretdione group containing polyisocyanates prepared in this fashion can be used to prepare polyurethanes.

EXAMPLES

EXAMPLE 1

Reacting 2,4-Toluene Diisocyanate 500 grams of 2,4-toluene diisocyanate and 200 grams of toluene were stirred at 20° C. and treated with 2.5 grams of 1,2-dimethylimidazole dissolved in 100 grams of toluene. Stirring continued at this temperature for 5 hours and the resulting suspension was allowed to stand for 16 hours. The solid product was washed with toluene and dried at 40° C. in a vacuum.

Composition 95 percent of a uretdione group containing polyisocyanate;

4 percent of unreacted 2,4-toluene diisocyanate; and 1 percent isocyanurate.

EXAMPLE 2

Reacting 4,4'-Diphenylmethane Diisocyanate

Following example 1, the 4,4'-diphenylmethane diisocyanante dissolved was treated at 50° C. with the dissovled 1,2-dimethylimidazole. Stirring continued for 2 hours at 50° C. and the suspension was allowed to stand at room temperature overnight.

Composition 85 percent of a uretdione group containing polyisocyanate;

13 percent of unreacted 4,4-diphenylmethane diisocyante; and 2 percent isocyanurate.

I and/or we claim:

1. A process for the preparations of uretdione group containing polyisocyanates, comprising reacting monomeric aromatic diisocyanates in the presence of 1,2-dimethylimidazole as a catalyst in an inert organic solvent wherein the weight ratio of solvent to diisocyanate lies in a range of from 0.1:1 to 2:1.

2. The process of claim 1 wherein toluene is used as said solvent.

* * * * *